(12) United States Patent
Foley

(10) Patent No.: US 6,220,706 B1
(45) Date of Patent: Apr. 24, 2001

(54) METHOD AND APPARATUS FOR DETERMINING POSITION OF AN EYE

(75) Inventor: James P. Foley, Fremont, CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/502,063

(22) Filed: Feb. 10, 2000

(51) Int. Cl.[7] .................................................. A61B 3/14
(52) U.S. Cl. ............................................................ 351/209
(58) Field of Search ................................... 351/205, 209, 351/210, 221; 606/10, 13, 4, 5, 6; 382/115

(56) References Cited

U.S. PATENT DOCUMENTS

| | | | |
|---|---|---|---|
| 4,102,564 | 7/1978 | Michael | 351/7 |
| 4,145,122 | 3/1979 | Rinard et al. | 351/7 |
| 4,209,252 | 6/1980 | Arditty et al. | 356/4 |
| 4,387,974 | 6/1983 | Marshall et al. | 351/210 |
| 4,436,389 | 3/1984 | Sano | 351/208 |
| 4,511,227 | 4/1985 | Nunokawa et al. | 351/208 |
| 4,678,297 | 7/1987 | Ishikawa et al. | 351/208 |
| 4,702,575 | 10/1987 | Breglia | 351/210 |
| 4,735,498 | 4/1988 | Udden et al. | 351/210 |
| 4,813,778 | 3/1989 | Madate et al. | 351/208 |
| 4,902,121 | 2/1990 | Shian | 351/208 |
| 5,371,558 | 12/1994 | Kohayakawa | 351/208 |
| 5,406,074 | 4/1995 | Grisell | 250/221 |
| 5,502,519 | 3/1996 | Hosoi | 351/204 |
| 5,502,521 | 3/1996 | Katou | 351/221 |
| 5,532,769 | 7/1996 | Miwa et al. | 351/205 |
| 5,557,350 | 9/1996 | Yano | 351/208 |
| 5,596,377 | 1/1997 | Yano | 351/211 |
| 5,604,818 | 2/1997 | Saitou et al. | 382/128 |
| 5,644,375 | 7/1997 | Suzuki | 351/208 |
| 5,680,196 | 10/1997 | Masuda | 351/208 |
| 5,682,224 | 10/1997 | Takagi et al. | 351/208 |
| 5,694,197 | 12/1997 | Tsukada et al. | 351/206 |
| 5,764,341 | 6/1998 | Fujieda et al. | 351/221 |
| 5,765,045 | 6/1998 | Takagi et al. | 396/51 |
| 5,818,954 | * 10/1998 | Tomono et al. | 382/115 |
| 5,865,832 | * 2/1999 | Knopp et al. | 606/10 |

* cited by examiner

Primary Examiner—George Manuel
(74) Attorney, Agent, or Firm—Michael B. Einschlag

(57) ABSTRACT

An embodiment of the present invention is an apparatus to determine position of an eye that includes: (a) two off-axis, radiation emitter-photodetector pairs, wherein an emitter of a pair is disposed to transmit radiation toward the eye and a photodetector of the pair is disposed to receive radiation reflected by the eye; and (b) a controller that analyzes output from the photodetectors to determine the position of the eye.

17 Claims, 3 Drawing Sheets

BALANCED
ILLUMINATION
CENTRED
VERTEX

UNBALANCED
ILLUMINATION
OFFSET
VERTEX

|  | QUAD 120 | QUAD 130 |
|---|---|---|
| FIG.3B CENTRED VERTEX |  |  |
| FIG.3C X VERTEX OFFSET: |  |  |
| FIG.3D Y VERTEX OFFSET: |  |  |
| FIG.3E Z VERTEX OFFSET: |  |  |
| FIG.3F |  |  |

METHOD AND APPARATUS FOR DETERMINING POSITION OF AN EYE

TECHNICAL FIELD OF THE INVENTION

The present invention pertains to the field of determining position of an eye, for example, a human eye.

BACKGROUND OF THE INVENTION

A common design issue associated with ophthalmic instruments is that significant diagnostic errors can be introduced whenever a patient's eye is not positioned within predetermined bounds. Some prior art ophthalmic instruments rely on an operator's judgment and skill to visually monitor the position of the patient's eye, and manually to place it in an "acceptable" location. An Acuitus Model 5000 available from Carl Zeiss, Inc. of Dublin, Calif. is one such manually positioned, prior art ophthalmic instrument. In using this ophthalmic instrument, an operator must judge the position of the patient's eye using a video image thereof. To do this, the operator centers the pupil of the patient's eye on a video screen; the operator infers the position of the eye from the degree of focus of the video image of the pupil. As can be readily appreciated from this, eye position is problematic because the degree of focus of the video image is subjective, and it is generally not very sensitive. Thus, some error in eye position is inevitable in such a manually positioned ophthalmic instrument because of variation in operator judgment and skill.

As is also well known to those of ordinary skill in the art, ophthalmic instruments can use eye position measurement data to help correct for diagnostic measurement errors associated with residual eye position offset errors. For example, one type of prior art ophthalmic instrument uses eye position measurement data to compensate for refractor errors caused, for example, by range offset. Range offset refers to errors in positioning the instrument in the correct position along the patient's line of sight. However, despite an ophthalmic instrument's being designed to minimize diagnostic measurement errors caused by eye position offset errors, some eye position offset error sensitivity still occurs.

As one can readily appreciate from the above, a need exists in the art for a method and apparatus to determine position of an eye.

SUMMARY OF THE INVENTION

Embodiments of the present invention advantageously satisfy the above-identified need in the art and provide method and apparatus to determine position of an eye.

A preferred embodiment of the present invention is an apparatus to determine position of an eye that comprises: (a) two off-axis, radiation emitter-photodetector pairs, wherein an emitter of a pair is disposed to transmit radiation toward the eye and a photodetector of the pair is disposed to receive radiation reflected by the eye; and (b) a controller that analyzes output from the photodetectors to determine the position of the eye.

In addition, one embodiment of the present invention is a simple, modular, stand-alone alternative to video image processing schemes, which simple, modular, stand-alone alternative does not impact the design of the rest of an ophthalmic instrument with which it is associated and is easy to manufacture and install. Advantageously, the one embodiment provides good accuracy, sensitivity, range, and cycle rate in a modular package.

BRIEF DESCRIPTION OF THE FIGURE

FIGS. 3A–3F illustrate the manner in which quadrant photodetectors used to fabricate an embodiment of the present invention operate to indicate corneal vertex displacement of a patient's eye.

DETAILED DESCRIPTION

Figure 1:
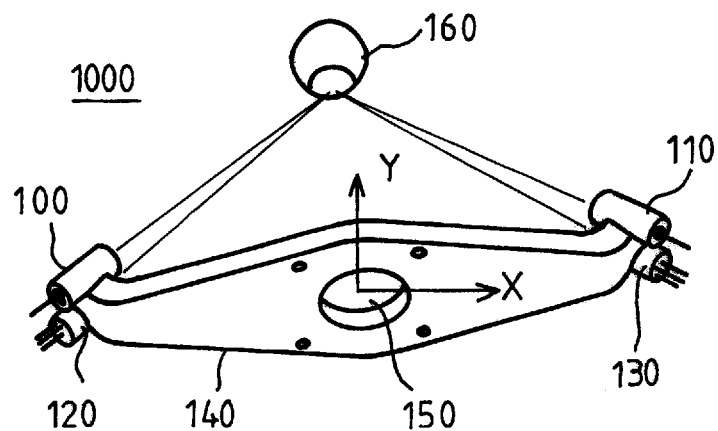
FIG. 1 shows a diagram of an embodiment of the present invention to detect vertex position of a patient's eye.

FIG. 1 shows embodiment 1000 of the present invention. As shown in FIG. 1, embodiment 1000 comprises two collimated radiation sources, infrared ("IR") emitters 100 and 110, and two radiation detectors, IR quadrant photodetectors 120 and 130, all of which are held in fixture 140. As further shown in FIG. 1, frame 140 is configured with viewport 150 for use by an ophthalmic instrument with which embodiment 1000 may be used in viewing a patient's eye 160. As still further shown in FIG. 1, emitters 100 and 110 and detectors 120 and 130 are configured as two IR emitter-detector pairs (pair 1 comprises off axis IR emitter 100 and diagonally opposed off-axis quadrant photodetector 130 and pair 2 comprises off axis IR emitter 110 and diagonally opposed off-axis quadrant photodetector 120).

Embodiment 1000 also comprises electronic circuitry (not shown for clarity and ease of understanding the present invention) that: (a) drives emitters 100 and 110 in accordance with any one of a number of methods that are well known to those of ordinary skill in the art; (b) reads outputs from quadrant photodetectors 120 and 130 in accordance with any one of a number of methods that are well known to those of ordinary skill in the art; and (c) interfaces with a controller (not shown) in accordance with any one of a number of methods that are well known to those of ordinary skill in the art. As is well known to those of ordinary skill in the art, electronic circuitry that performs these functions can also be a part of the controller, which controller can be, for example, a computer. In accordance with a preferred embodiment of the present invention, and as will be described in detail below, a software routine that operates in a manner to be described in detail below converts outputs from detectors 120 and 130 to an X,Y,Z position of the vertex of the cornea of patient's eye 160.

Figure 2:
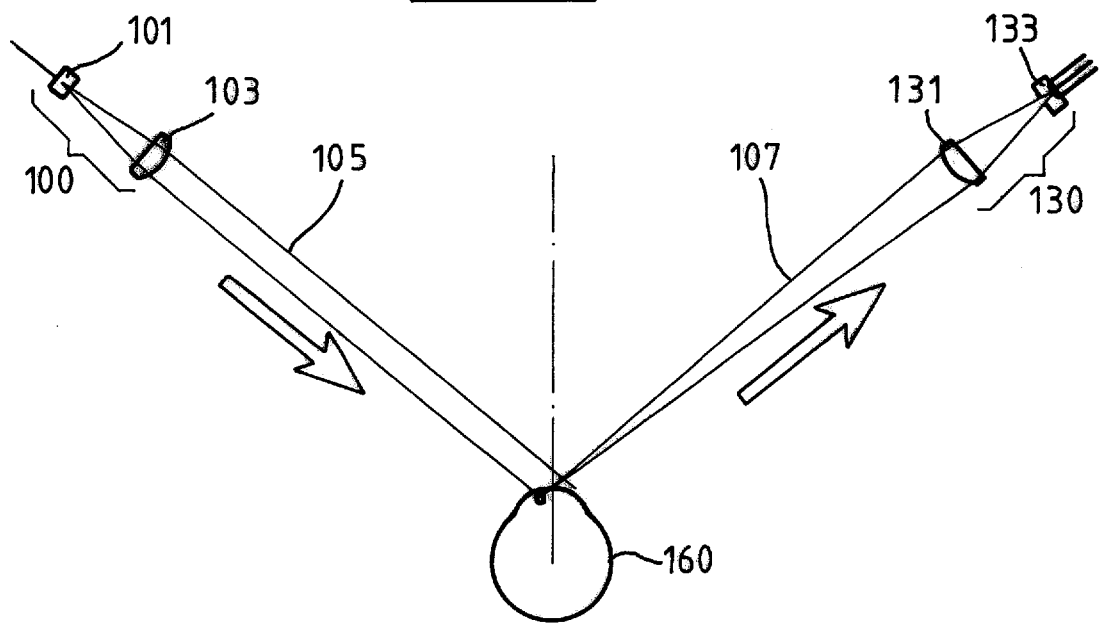
FIG. 2 shows a diagram of light paths involved in using an embodiment of the present invention.

FIG. 2 shows a diagram of light paths involved in using embodiment 1000 of the present invention for emitter-detector pair 1 which comprises off axis IR emitter 100 and diagonally opposed, off-axis, quadrant photodetector 130. As shown in FIG. 2, patient's eye 160 is disposed at a predetermined location with respect to fixture 150 (not shown in FIG. 2) by use of head seating fixture (not shown), which predetermined location provides placement of the cornea of the patient's eye at a nominal corneal position (all of this being done in accordance with any one of a number of methods which are well known to those of ordinary skill in the art). In conjunction with this, the patient may be asked to gaze at a fixation device to provide a reasonably steady choice for a nominal position. The fixation device may be fabricated in accordance with any one of a number of methods that are well known to those of ordinary skill in the art.

As further shown in FIG. 2, collimated IR emitter 100 comprises source LED 101 and lens system 103, and quadrant photodetector 130 comprises lens system 131 and photodetector 133. In accordance with a preferred embodiment of the present invention, lens systems 103 and 131 are configured so that IR emitter 100 and quadrant photodetector 130 have narrow fields-of-view; both of which fields of view are centered on the nominal corneal vertex position. As shown in FIG. 2, radiation beam 105 emitted by LED 101 is directed to impinge upon patient's eye 160 and, after reflection thereby, is captured (as radiation beam 107) by photodetector 133. In addition, fixture 150 is designed in accordance with any one of a number of methods that are well known to those of ordinary skill in the art so that quadrant photodetector 130 sees an image of IR emitter 100 along a line-of-sight that passes through the nominal vertex of the cornea of patient's eye 160.

As can readily be appreciated by one of ordinary skill in the art, a change in position of the vertex of the cornea of patient's eye 160 will produce a related change in the line-of-sight between the vertex of the cornea of patient's eye 160 and the quadrant photodetectors of embodiment 1000. In accordance with the present invention, output from each of quadrant photodetectors 120 and 130 enables the position of the vertex of the cornea to be measured in two dimensions. Then, in accordance with the present invention, and as will be described in detail below, measurements of the line-of-sight using outputs from both quadrant photodetectors 120 and 130 are combined to measure the vertex of the cornea in three dimensions (the X,Y,Z position). As one can readily appreciate, measurement of the vertex of the cornea in three dimensions is made possible because outputs from quadrant photodetectors 120 and 130, respectively, measure lines-of-sight from two different points of reference.

Figure 3A:
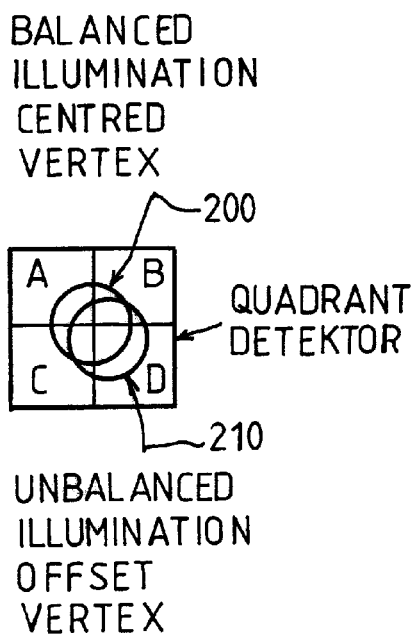
Figure 3A:
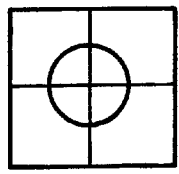
Figure 3A:
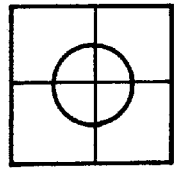
Figure 3A:
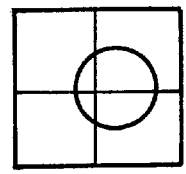
Figure 3A:
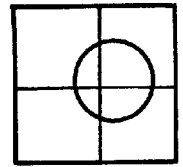
Figure 3A:
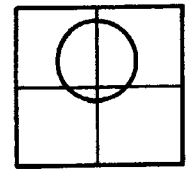
Figure 3A:
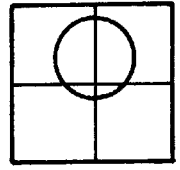
Figure 3A:
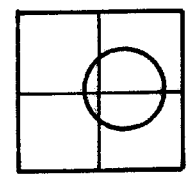
Figure 3A:
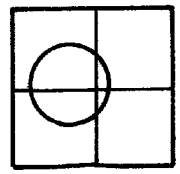
Figure 3A:
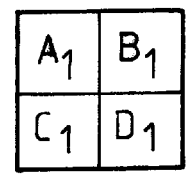
Figure 3A:
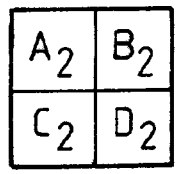

FIGS. 3A–3F illustrate the manner in which quadrant photodetectors used to fabricate embodiment 1000 of the present invention operate to indicate corneal vertex displacement of patient's eye 160. As shown in FIG. 3A, when one of quadrant photodetectors 120 and 130 receives radiation reflected from a centered corneal vertex, radiation pattern 200 is balanced, i.e., equal illumination is received in the four quadrants of the photodetector. As further shown in FIG. 3A, when one of quadrant photodetectors 120 and 130 receives radiation reflected from an offset corneal vertex, radiation pattern 210 is unbalanced, i.e., there is unequal illumination in the four quadrants of the detector. FIG. 3B shows the illumination received by quadrant photodetectors 120 and 130, respectively, for a centered corneal vertex. FIG. 3C shows the illumination received by quadrant photodetectors 120 and 130, respectively, for a corneal vertex with an X offset. FIG. 3D shows the illumination received by quadrant photodetectors 120 and 130, respectively, for a corneal vertex with an Y offset. FIG. 3E shows the illumination received by quadrant photodetectors 120 and 130, respectively, for a corneal vertex with an Z offset.

In accordance with a preferred embodiment of the present invention, quadrant photodetectors 120 and 130 are initially aligned to a nominal corneal vertex position, i.e., a position at which both quadrant photodetectors 120 and 130 exhibit a bias which is substantially zero or which differs therefrom by a predetermined amount. For example, this may be done by placing an artificial eye, for example, a glass eye, at a nominal origin (for example, 0,0,0) to align the apparatus. Then, as will described in detail below, in accordance with the present invention, horizontal and vertical biases of quadrant photodetectors 120 and 130 provide a measure of X,Y,Z displacement from the nominal corneal vertex position with high sensitivity. Advantageously, in accordance with the present invention, the method used to determine the position of the corneal vertex is insensitive to the radius of curvature of the cornea.

FIG. 3F shows how regions A, B, C, and D are defined for quadrant photodetectors 120 and 130. Using these definitions, the horizontal bias of quadrant photodetector 120 is given by:

$$H_1 = \frac{(A_1 + C_1) - (B_1 + D_1)}{(A_1 + B_1 + C_1 + D_1)}$$

and the vertical bias of quadrant photodetector 120 is given by:

$$V_1 = \frac{(A_1 + B_1) - (C_1 + D_1)}{(A_1 + B_1 + C_1 + D_1)}$$

Likewise, the horizontal bias of quadrant photodetector 130 is given by:

$$H_2 = \frac{(A_2 + C_2) - (B_2 + D_2)}{(A_2 + B_2 + C_2 + D_2)}$$

and the vertical bias of quadrant photodetector 130 is given by:

$$V_2 = \frac{(A_2 + B_2) - (C_2 + D_2)}{(A_2 + B_2 + C_2 + D_2)}$$

In accordance with the present invention, for "small" displacements, the X,Y,Z coordinates of the corneal vertex are linearly related to the horizontal and vertical biases of quadrant photodetectors 120 and 130. For the simple case shown in FIGS. 3C through 3E:

$$X = C_X(H_1 + H_2)$$

$$Y = C_Y(V_1 + V_2)$$

$$Z = C_Z(H_1 - H_2)$$

where $C_X$, $C_Y$, and $C_Z$ are constants that are determined by geometry and/or calibration in accordance with any one of a number of methods that are well known to those of ordinary skill in the art.

In a more general case, quadrant photodetectors 120 and 130 may be oriented with an arbitrary polar orientation. In such a case, the X,Y,Z coordinates of the corneal vertex are given by the following matrix relationship:

$$\begin{vmatrix} X \\ Y \\ Z \end{vmatrix} = \begin{vmatrix} C_{XH1} & C_{XV1} & C_{XH2} & C_{XV2} \\ C_{YH1} & C_{YV1} & C_{YH2} & C_{YV2} \\ C_{ZH1} & C_{ZV1} & C_{ZH2} & C_{ZV2} \end{vmatrix} \begin{vmatrix} H_1 \\ V_1 \\ H_2 \\ V_2 \end{vmatrix}$$

where $C_{XH1}$, $C_{YH1}$, $C_{ZH1}$, $C_{XV1}$, $C_{YV1}$, $C_{ZV1}$, $C_{XH2}$, $C_{YH2}$, $C_{ZH2}$, $C_{XV2}$, $C_{YV2}$, and $C_{ZV2}$ are constants that are determined by geometry and/or calibration in accordance with any one of a number of methods that are well known to those of ordinary skill in the art.

In accordance with a further embodiment of the present invention, cross-talk between emitter-photodetector pairs (100, 130) and (110, 120), respectively, can be minimized by alternately running only one emitter-photodetector pair at a time in accordance with signals that are generated in the electronic circuitry in accordance with any one of a number of methods that are well known to those of ordinary skill in the art. In addition, in a still further embodiment of the present invention, the electronic circuitry includes synchronous detection apparatus that operates in accordance with any one of a number of methods that are well known to those of ordinary skill in the art to reject unwanted signals in the photodetectors. For example, in accordance with such an embodiment, LED emitters 100 and 110 do not operate continuously, but flash in response to input from energizer portions of electronic circuitry which are fabricated in accordance with any one of a number of methods that are well known to those of ordinary skill in the art. Then, in accordance with the present invention, photodetector inputs are analyzed at times which correspond to times at which radiation reflected from the patient's eye is expected to be received, which times can be readily synchronized with the times during which the emitters are energized.

Advantageously, in accordance with the present invention, emitters 100 and 110 are configured so that on-axis images thereof, i.e., images that are reflected from patient's eye 160 and pass through viewport 150 of frame 140 are minimized. This is done to reduce interference with ophthalmic instruments with which embodiments of the present invention are used.

The output from embodiment 1000 which measures the X,Y,Z position data associated with the corneal vertex can be used to cause an ophthalmic instrument to make measurements whenever the vertex is sufficiently close to a predetermined position or the vertex position measurement data may be supplied to the ophthalmic instrument for use in determining or correcting diagnostic errors produced thereby.

In addition, the output from embodiment 1000 which measures the X,Y,Z position data associated with the corneal vertex can be used to cause an motorized system to drive a servomechanism to move the corneal vertex toward a predetermined position, or to cause a feedback cue to be given to an operator to prompt corrective positioning action.

Figure 4:
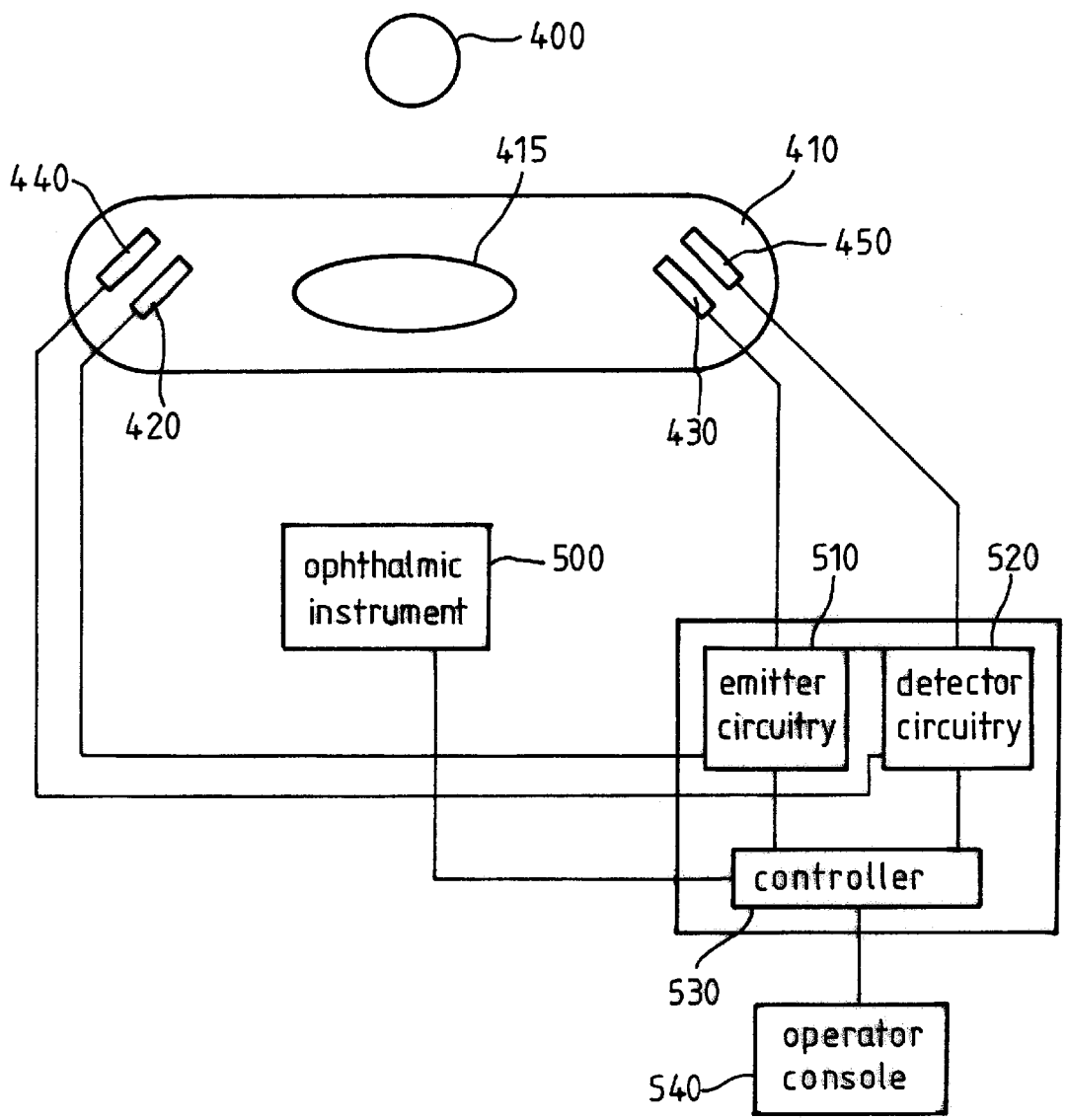
FIG. 4 shows a block diagram of an embodiment of the present invention used in conjunction with an ophthalmic instrument.

FIG. 4 shows a block diagram of an embodiment of the present invention used in conjunction with an ophthalmic instrument. As shown in FIG. 4, emitter-photodetector pairs (420, 450) and (430, 440) are affixed to frame 410 which provides a line of sight between patient's eye 400 and ophthalmic instrument 500. As shown in FIG. 4, emitters 420 and 430 are connected to emitter circuitry 510, which emitter circuitry 510 operates in response to signals from controller 530 to transmit electrical pulses to energize emitters 420 in accordance with any one of a number of methods that are well known to those of ordinary skill in the art. As further shown in FIG. 4, photodetectors 440 and 450 receive radiation reflected from patient's eye 400 and transmit signals to detector circuitry 520, which detector circuitry 520 transmits detector signals to controller 530 in accordance with any one of a number of methods that are well known to those of ordinary skill in the art. Controller 530 analyzes the detection signals in accordance with the methods described above. Further, the synchronization of emitter output and detector signal analysis may be performed by signals sent from controller 530 to emitter circuitry 510 and detector circuitry 520. Alternatively, the synchronization may be performed within controller 530.

As discussed above, controller 530 may send information to be displayed on operator console 540 in accordance with any one of a number of methods that are well known to those of ordinary skill in the art, which information indicates a corneal vertex position and which information may further indicate a position correction movement that may be used to alter the position to a predetermined position. Alternatively, controller 530 may send a signal to a positioning device (not shown) for moving the position of either patient's eye 400 or ophthalmic instrument 500 in accordance with any one of a number of methods that are well known to those of ordinary skill in the art. Lastly, if controller 530 determines that the position of the corneal vertex of patient's eye 400 is at a predetermined position, controller 530 can sent a message in accordance with any one of a number of methods that are well known to those of ordinary skill in the art to ophthalmic instrument 500. In response, ophthalmic instrument can take an appropriate action such as making a measurement of patient's eye 400.

Those skilled in the art will recognize that the foregoing description has been presented for the sake of illustration and description only. As such, it is not intended to be exhaustive or to limit the invention to the precise form disclosed. For example, although embodiments of the present invention were discussed in terms of using quadrant photodetectors, embodiments may be fabricated using, for example, video detectors such as for example, CCD video detectors. In such a case, the video photodetector outputs are analyzed in accordance with any one of a number of methods that are well known to those of ordinary skill in the art to determine a horizontal and vertical bias of the radiation reflected by the patient's eye.

What is claimed is:

1. An apparatus to determine (X,Y,Z) coordinates of position of a vertex of a cornea of an eye which comprises:
   two off-axis, radiation emitter-photodetector pairs,
   wherein an off-axis emitter of a pair is disposed to transmit radiation toward the eye and an off-axis photodetector of the pair is disposed to receive radiation reflected by the eye; and
   a controller that analyzes output from the photodetectors to determine the (X,Y,Z) coordinates of position of the eye.

2. The apparatus of claim 1 wherein the photodetectors are quadrant photodetectors.

3. The apparatus of claim 2 wherein the emitters are sources of collimated radiation.

4. The apparatus of claim 3 wherein the emitters comprise infrared LEDs.

5. The apparatus of claim 2 wherein the controller analyzes output from the photodetectors to determine a horizontal and vertical bias of the radiation reflected by the eye to determine the (X,Y,Z) coordinates of position of the eye.

6. The apparatus of claim 1 wherein the photodetectors are CCD photodetectors and the controller analyzes output from the photodetectors to determine a horizontal and vertical bias of the radiation reflected by the eye to determine the (X,Y,Z) coordinates of position of the eye.

7. The apparatus of claim 6 wherein the emitters are sources of collimated infrared radiation.

8. The apparatus of claim 1 wherein the emitters and the photodetectors have narrow fields-of-view that are centered on a predetermined position by a frame.

9. The apparatus of claim 1 wherein the emitters are disposed to transmit radiation toward the same portion of the eye.

10. The apparatus of claim 9 wherein a first line between the first emitter-photodetector pair and a second line between the second emitter-photodetector pair are not parallel.

11. The apparatus of claim 1 wherein the emitters are disposed far enough off-axis so that substantially no on-axis images thereof are reflected from the eye.

12. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller causes one emitter-photodetector pair to run at a time, whereby cross-talk between the emitter-photodetector pairs is minimized.

13. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller synchronizes the emitter-photodetector pair operation.

14. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller sends a signal to an ophthalmic instrument whenever the position is substantially close to a predetermined position.

15. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller sends a signal to a motorized system to drive a servomechanism to move the apparatus or eye or to cause a feedback cue to be given to an operator.

16. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller analyzes output from the photodetectors to determine a horizontal and vertical bias of the radiation reflected by the eye to determine the (X,Y,Z) coordinates of position of the eye and wherein:

$$X = C_X(H_1 + H_2)$$

$$Y = C_Y(V_1 + V_2)$$

$$Z = C_Z(H_1 - H_2);$$

wherein $H_1$ is a horizontal bias from the first photodetector, $V_1$ is a vertical bias from the first photodetector, $H_2$ is a horizontal bias from the second photodetector, and $V_2$ is a vertical bias from the second photodetector.

17. An apparatus to determine (X,Y,Z) coordinates of position of an eye which comprises:

two off-axis, radiation emitter-photodetector pairs;

wherein an off-axis emitter of a pair is disposed to transmit radiation toward the eye and an off-axis photodetector of the pair is disposed to receive radiation reflected by the eye; and a controller that analyzes output from the photodetectors to determine the (X,Y,Z) coordinates of position of the eye; wherein the controller analyzes output from the photodetectors to determine a horizontal and vertical bias of the radiation reflected by the eye to determine the (X,Y,Z) coordinates of position of the eye and wherein:

$$X = C_{XH1}H_1 + C_{XV1}V_1 + C_{XH2}H_2 + C_{XV2}V_2$$

$$Y = C_{YH1}H_1 + C_{YV1}V_1 + C_{YH2}H_2 + C_{YV2}V_2$$

$$Z = C_{ZH1}H_1 + C_{ZV1}V_1 + C_{ZH2}H_2 + C_{ZV2}V_2;$$

wherein $H_1$ is a horizontal bias from the first photodetector, $V_1$ is a vertical bias from the first photodetector, $H_2$ is a horizontal bias from the second photodetector, and $V_2$ is a vertical bias from the second photodetector.

* * * * *